US008295941B2

(12) United States Patent
Hyde et al.

(10) Patent No.: US 8,295,941 B2
(45) Date of Patent: Oct. 23, 2012

(54) SYSTEMS CONFIGURED TO POWER AT LEAST ONE DEVICE DISPOSED IN A LIVING SUBJECT, AND RELATED APPARATUSES AND METHODS

(75) Inventors: Roderick A. Hyde, Redmond, WA (US); Muriel Y. Ishikawa, Livermore, CA (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 730 days.

(21) Appl. No.: 12/378,152

(22) Filed: Feb. 11, 2009

(65) Prior Publication Data

US 2010/0070003 A1 Mar. 18, 2010

Related U.S. Application Data

(63) Continuation-in-part of application No. 12/283,911, filed on Sep. 15, 2008, which is a continuation-in-part of application No. 12/316,811, filed on Dec. 15, 2008.

(51) Int. Cl.
*A61N 1/00* (2006.01)

(52) U.S. Cl. .......................................................... 607/61

(58) Field of Classification Search .................... 607/33, 607/60, 61
See application file for complete search history.

(56) References Cited

U.S. PATENT DOCUMENTS

| | | | | |
|---|---|---|---|---|
| 5,320,098 | A | 6/1994 | Davidson | |
| 5,387,259 | A * | 2/1995 | Davidson | 600/310 |
| 6,898,464 | B2 | 5/2005 | Edell et al. | |
| 2006/0139000 | A1 | 6/2006 | Bailey et al. | |
| 2007/0027505 | A1 | 2/2007 | Ginggen | |
| 2009/0171404 | A1 | 7/2009 | Irani et al. | |

OTHER PUBLICATIONS

Roderick A. Hyde et al., U.S. Appl. No. 12/283,911, filed Sep. 15, 2008, "Systems Configured to Transmit Optical Power Signals Transdermally Out of a Living Subject, and Devices and Methods".
Roderick A. Hyde et al., U.S. Appl. No. 12/316,811, filed Dec. 15, 2008, "Systems Configured to Locate a Photonic Device Disposed in a Living Subject, and Related Apparatuses and Methods".

* cited by examiner

*Primary Examiner* — Eric D. Bertram
(74) *Attorney, Agent, or Firm* — Workman Nydegger

(57) ABSTRACT

Embodiments disclosed herein are directed to systems configured to power at least one device disposed in a living subject, apparatuses configured to be disposed in a living subject and export power stored in an energy-storage device, and related methods of powering at least one device disposed in the living subject.

22 Claims, 6 Drawing Sheets

SYSTEMS CONFIGURED TO POWER AT LEAST ONE DEVICE DISPOSED IN A LIVING SUBJECT, AND RELATED APPARATUSES AND METHODS

RELATED APPLICATIONS

For purposes of the USPTO extra-statutory requirements, the present application constitutes a continuation-in-part of U.S. patent application Ser. No. 12/283,911, entitled SYSTEMS CONFIGURED TO TRANSMIT OPTICAL POWER SIGNALS TRANSDERMALLY OUT OF A LIVING SUBJECT, AND DEVICES AND METHODS, naming RODERICK A. HYDE, MURIEL Y. ISHIKAWA, DENNIS J. RIVET, ELIZABETH A. SWEENEY, LOWELL L. WOOD, J R., AND VICTORIA Y. H. WOOD as inventors, filed 15 Sep. 2008, which is currently co-pending, or is an application of which a currently co-pending application is entitled to the benefit of the filing date.

For purposes of the USPTO extra-statutory requirements, the present application constitutes a continuation-in-part of U.S. patent application No. 12/316,811, entitled SYSTEMS CONFIGURED TO LOCATE A PHOTONIC DEVICE DISPOSED IN A LIVING SUBJECT, AND RELATED APPARATUSES AND METHODS, naming RODERICK A. HYDE, MURIEL Y. ISHIKAWA, DENNIS J. RIVET, LOWELL L. WOOD, JR., AND VICTORIA Y.H. WOOD as inventors, filed 15 Dec. 2008, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In an embodiment, a system includes an optical-electrical converter configured to be disposed within a living subject, receive one or more optical power signals transmitted transdermally into the living subject, and convert the one or more optical power signals into electrical energy. The system further includes a power conditioning unit configured to be disposed within a living subject and coupled to the optical-electrical converter to receive at least a portion of the electrical energy therefrom. The power conditioning unit may be further configured to selectively condition the received at least a portion of the electrical energy into one or more electrical power signals.

In an embodiment, a method includes receiving one or more optical power signals that are transmitted transdermally into a living subject, with an optical-electrical converter disposed within the living subject. The method also includes converting the one or more optical power signals into electrical energy using the optical-electrical converter. The method further includes selectively conditioning at least a portion of the electrical energy into one or more electrical power signals.

In an embodiment, a method includes transmitting one or more conditioning signals to a signal converter or a power conditioning unit disposed within a living subject. The method further includes transmitting one or more optical power signals transdermally into the living subject and to an optical-electrical converter disposed therein.

In an embodiment, a system includes an optical-electrical converter, an energy-storage device, and an electrical-optical converter. The optical-electrical converter may be configured to be disposed within a living subject, receive one or more first optical signals transmitted transdermally into the living subject, and convert the one or more first optical signals into electrical energy. The energy-storage device may be configured to be disposed within the living subject and coupled to the optical-electrical converter to receive at least a portion of the electrical energy therefrom. The energy-storage device may be further configured to store the at least a portion of the electrical energy received from the optical-electrical converter. The electrical-optical converter may be configured to be disposed within a living subject and coupled to the energy-storage device. The electrical-optical converter may be further configured to receive the at least a portion of the electrical energy from the energy-storage device and convert the at least a portion of the electrical energy into one or more second optical signals.

In an embodiment, a method includes receiving one or more first optical signals that are transmitted transdermally into a living subject, with an optical-electrical converter disposed within the living subject. The method also includes converting the one or more first optical signals into electrical energy with the optical-electrical converter. The method additionally includes storing at least a portion of the electrical energy in an energy-storage device disposed within the living subject. The method further includes converting at least a portion of the stored electrical energy into one or more second optical signals with an electrical-optical converter disposed within the living subject.

In an embodiment, an apparatus configured for disposal within a living subject includes an optical-electrical converter, an energy-storage device, and at least one power exporter. The optical-electrical converter may be configured to receive one or more optical power signals transmitted transdermally into the living subject and convert one or more optical power signals into electrical energy. The energy-storage device may be coupled to the optical-electrical converter to receive at least a portion of the electrical energy therefrom. The energy-storage device may be further configured to store the at least a portion of the electrical energy received from the optical-electrical converter. The at least one power exporter may be coupled to the energy-storage device to receive the at least a portion of the electrical energy and configured to transmit the at least a portion of the electrical energy.

In an embodiment, a system includes an optical-electrical converter, an energy-storage device, and at least one device. The optical-electrical converter may be configured to be disposed within a living subject, receive one or more optical power signals transmitted transdermally into the living subject, and convert one or more optical power signals into electrical energy. The energy-storage device may be configured to be disposed within the living subject and coupled to the optical-electrical converter to receive at least a portion of the electrical energy therefrom. The energy-storage device may be further configured to store the at least a portion of the electrical energy received from the optical-electrical converter. The at least one device may be configured to be disposed within the living subject, and further configured to be operably coupled to the energy-storage device to receive the at least a portion of the electrical energy therefrom.

In an embodiment, a method includes receiving one or more optical power signals that are transmitted transdermally into a living subject, with an optical-electrical converter disposed within the living subject. The method also includes storing electrical energy generated by the optical-electrical converter in an energy-storage device disposed within the living subject. The method further includes powering at least one device disposed within the living subject using at least a portion of the electrical energy.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other subject matter described herein will become apparent after reading the teachings set forth herein.

DETAILED DESCRIPTION

Figure 1A:
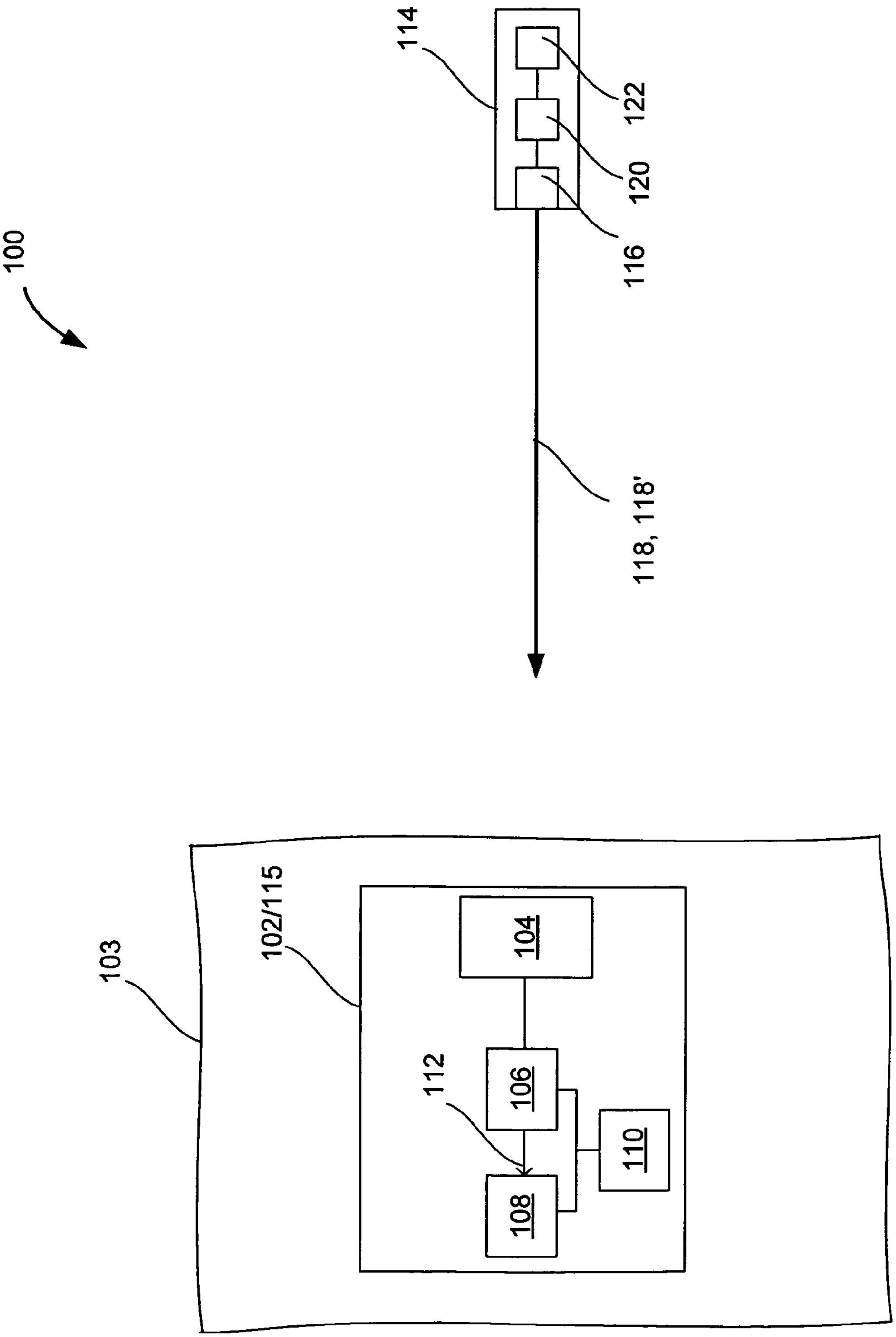
FIG. 1A is a functional block diagram of an embodiment of a system including an optical-electrical converter, and a power conditioning unit disposed within a living subject and configured to selectively condition electrical energy received from the optical-electrical converter.

Embodiments disclosed herein are directed to systems configured to power at least one device disposed in a living subject, apparatuses configured to be disposed in a living subject and export power stored in an energy-storage device, and related methods such as powering the at least one device disposed in the living subject. Other embodiments disclosed herein are directed to systems and methods for converting stored electrical energy to optical energy and transmitting such optical energy to a selected location within a living subject. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

FIG. 1A is a functional block diagram of an embodiment of a system 100 including an optical-electrical converter, and a power conditioning unit disposed within a living subject and configured to selectively condition electrical energy received from the optical-electrical converter. Referring to FIG. 1A, the system 100 includes a biocompatible apparatus 102 configured to be disposed within a living subject 103, such as being embedded, for example, in tissue, muscle, or bone of a human being. The apparatus 102 includes an optical-electrical converter 104 (e.g., one or more photodiodes), a power conditioning unit 106 coupled to receive and condition electrical energy received from the optical-electrical converter 104, at least one device 108 coupled to the power conditioning unit 106 to receive conditioned electrical energy therefrom, and control electrical circuitry 110 configured to control the operation of the at least one device 108 and distribution of the conditioned electrical energy thereto from the power conditioning unit 106.

The optical-electrical converter 104, power conditioning unit 106, at least one device 108, and control electrical circuitry 110 may be configured to be disposed in the living subject 103, such as by being sized for being disposed within the living subject 103 or biocompatible with the living subject 103. For example, the optical-electrical converter 104, power conditioning unit 106, at least one device 108, and control electrical circuitry 110 may be compactly enclosed in a biocompatible protective packaging 115 to package one or more components of the apparatus 102. In an embodiment, the optical-electrical converter 104, power conditioning unit 106, at least one device 108, and control electrical circuitry 110 may each be individually enclosed in separate biocompatible packaging sections.

The power conditioning unit 106 may include a DC-to-AC converter, an AC-to-DC converter, a DC-to-DC converter, or an AC-to-AC converter. For example, the DC-to-AC converter may convert the received electrical energy from a DC waveform to an AC waveform, the AC-to-DC converter may convert the received electrical energy from an AC waveform to a DC waveform, the DC-to-DC converter may convert the received electrical energy from a first DC waveform to a different second DC waveform, and the AC-to-AC converter may convert the received electrical energy from a first AC waveform to a different second AC waveform.

The at least one device 108 may be configured as at least one of a drug delivery device, a micro-electro-mechanical device, a bone extension device, a biosensor, a heart pacemaker, a heart stimulator, a neurostimulator, or other suitable biomedical device. The control electrical circuitry 110 is configured to control distribution of electricity from the power conditioning unit 106 to the at least one device 110 as one or more conditioned electrical power signals 112 that power the at least one device 110. The control electrical circuitry 110 may be powered by its own dedicated power source or may be configured to use a small amount of power from a common energy-storage device (not shown) for power. The at least one device 108 may be spatially separate from and not a component of the optical-electrical converter 104. For example, the at least one device 108 may disposed in a different location of the living subject 103 and not packaged with the optical-electrical converter 104, power conditioning unit 106, and control electrical circuitry 110 and the at least one device 108 may not form part of the circuitry of the optical-electrical converter 104.

The system 100 may further include a selectively positionable external optical power device 114 (e.g., a hand-held device) located external to the living subject 103. The external optical power device 114 includes an optical power source 116 (e.g., one or more light-emitting diodes, lasers, or other suitable light-emitting devices) configured to output one or more optical power signals 118, control electrical circuitry 120 coupled to the optical power source 116, and a user interface 122 coupled to the control electrical circuitry 120. For example, the user interface 122 may be configured as a keypad, touch screen, or other suitable interface that allows the living subject 103 or other user to control the operation of the external optical power device 114.

Still referring to FIG. 1A, in operation, the optical power source 116 of the external optical power device 114 outputs the one or more optical power signals 118 as one or more electromagnetic beams at the living subject 103 that are transdermally transmitted through tissue of the living subject 103, through the biocompatible protective packaging 115, and received by the optical-electrical converter 104. For example, the one or more optical power signals 118 may exhibit at least one infrared or visible peak wavelength that is transdermally transmittable through tissue of the living subject 103. In an embodiment, the optical-electrical converter 104 may be configured to selectively convert specific wavelengths of the one or more optical power signals 118 to electrical energy.

The one or more optical power signals 118 received by the optical-electrical converter 104 are converted to electrical energy by the optical-electrical converter 104. At least a portion of the electrical energy may be transmitted to the power conditioning unit 106. The power conditioning unit 106 selectively conditions the received at least a portion of the electrical energy to generate the one or more conditioned electrical power signals 112, under the control of the control electrical circuitry 110, for powering the at least one device 108. For example, the power conditioning unit 106 may convert a DC waveform to an AC waveform, an AC waveform to a DC waveform, a DC waveform to a different DC waveform, or an AC waveform to a different AC waveform depending on the type of waveform of the received at least a portion of the electrical energy or the configuration of the power conditioning unit 106. In an embodiment, the one or more conditioned electrical power signals 112 exhibit a frequency selected to limit interference with other biomedical devices disposed in the living subject 103.

In an embodiment, the power conditioning unit 106 may selectively condition the at least a portion of the electrical energy received from the optical-electrical converter 104 in response to receiving conditioning instructions from the at least one device 108 or another device disposed in the living subject 103 separate from the at least one device 108. For example, the at least one device 108 may be configured to periodically or continuously output such conditioning instructions to the power conditioning unit 106 so that the power conditioning unit 106 conditions the at least a portion of the electrical energy in a manner most suitable for use by the at least one device 108.

As previously discussed, the optical-electrical converter 104, power conditioning unit 106, at least one device 108, and control electrical circuitry 110 may be enclosed in the biocompatible protective packaging 115 that is at least partially transparent to the one or more optical power signals 118 output by the external optical power device 114. The biocompatible protective packaging 115 may be formed from a number of different biocompatible polymeric materials, such as at least one of polyxylene, polyethylene, poly(ethylene oxide), polyurethane, or poly(butylene terephthalate). The biocompatible protective packaging 115 may also be formed from a number of different biocompatible ceramics, such as silicate-based ceramics. In an embodiment, the biocompatible protective packaging 115 may be in the form of a biocompatible coating made from at least one of the aforementioned biocompatible polymeric or ceramic materials and formed over a relatively less biocompatible housing that provides structural support for the biocompatible coating or a housing formed from at least one of the aforementioned biocompatible materials.

Figure 1B:
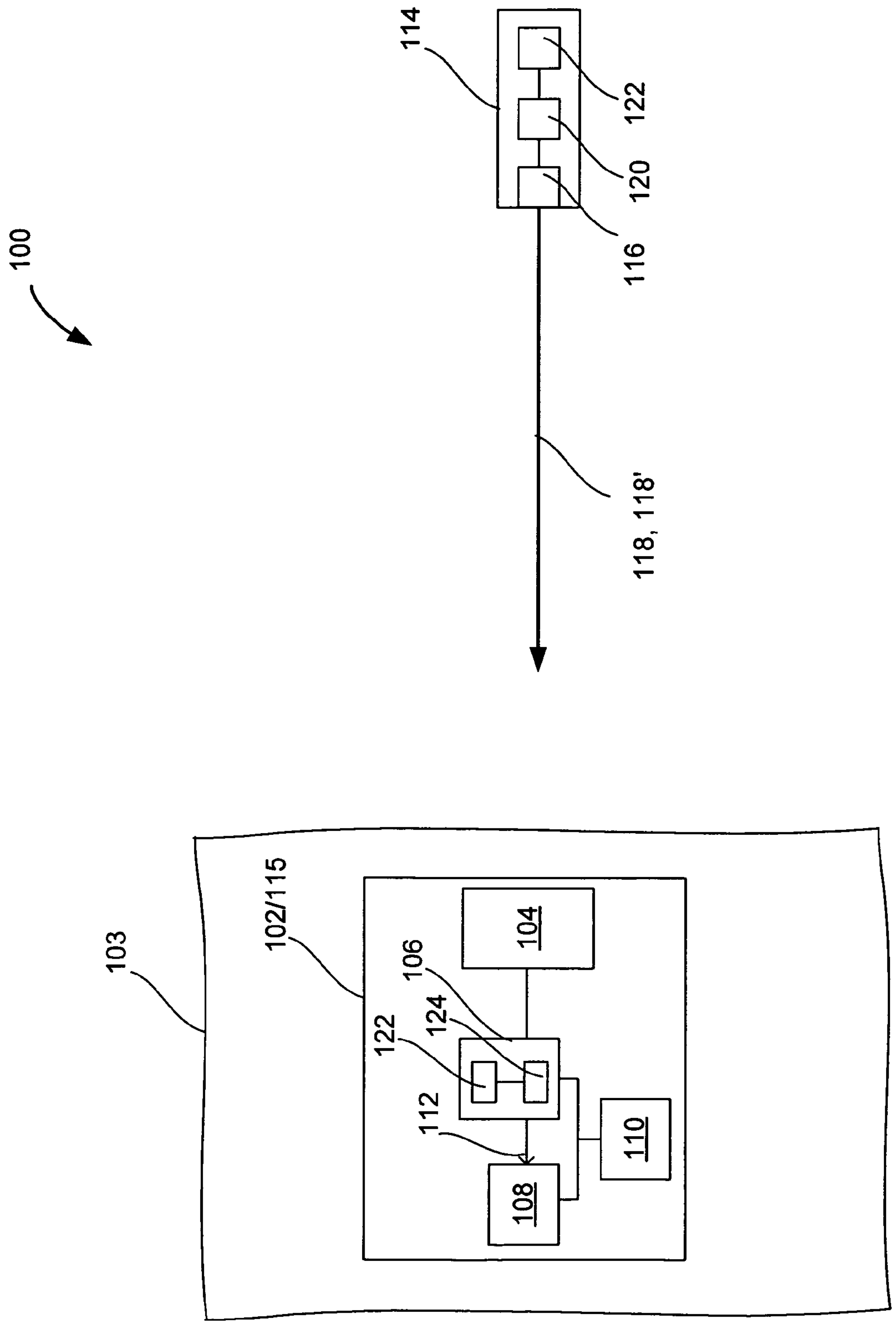
FIG. 1B is a functional block diagram of the system shown in FIG. 1A, with the power conditioning unit configured to selectively condition electrical energy received from the optical-electrical converter responsive to one or more transdermally transmitted conditioning signals.

Referring to FIG. 1B, in an embodiment, the power conditioning unit 106 may be configured to selectively condition the received electrical energy in response to receiving one or more conditioning signals transmitted transdermally into the living subject 103 thereto. For example, the power conditioning unit 106 may include an optical-electrical signal converter 124 coupled to control electrical circuitry 126 that controls the operation of the power conditioning unit 106. In such an embodiment, the optical power source 116 of the external optical power device 114 may be configured to output one or more conditioning signals 118' that are transmitted transdermally into the living subject 103, received by the power conditioning unit 106, and converted by the optical-electrical signal converter 124 to one or more electrical conditioning signals (not shown). Under control of the control electrical circuitry 126, the power conditioning unit 106 may selectively condition the electrical energy received from the optical-electrical signal converter 124 according to instructions encoded in the one or more electrical conditioning signals. In an embodiment, the one or more conditioning signals 118' may be transmitted substantially simultaneous with transmission of the one or more optical power signals 118. In an embodiment, the one or more conditioning signals 118' may be transmitted prior to transmission of the one or more optical power signals 118. In an embodiment, the one or more conditioning signals 118' may exhibit at least one of a peak wavelength, polarization, or time-profile that is different than that of the one or more optical power signals 118.

In an embodiment, the optical-electrical signal converter 124 of the power conditioning unit 106 may be replaced with a radio-frequency receiver device. In such an embodiment, the one or more conditioning signals may be outputted from a separate radio-frequency transmitter or a radio-frequency transmitter integrated with the external optical power device 114 as one or more radio-frequency signals encoding conditioning instructions for the power conditioning unit 106. The radio-frequency receiver device outputs one or more conditioning electrical signals to the power conditioning unit 106 in response to receiving the one or more radio-frequency signals. In an embodiment, an ultrasound transducer or other signal converter may replace the optical-electrical signal converter 124 and convert one or more ultrasound conditioning signals to one or more electrical conditioning signals.

In the illustrated embodiment shown in FIG. 1B, the power conditioning unit 106 includes a dedicated optical-electrical signal converter 124 that receives and converts the one or more conditioning signals 118' to one or more electrical conditioning signals. However, in another embodiment, the optical-electrical converter 104 may convert the one or more conditioning signal 118' to the one or more electrical conditioning signals encoding conditioning instructions, which are transmitted to the power conditioning unit 106 prior to the power conditioning unit 106 conditioning the electrical energy converted from the one or more optical power signals 118.

Figure 2:
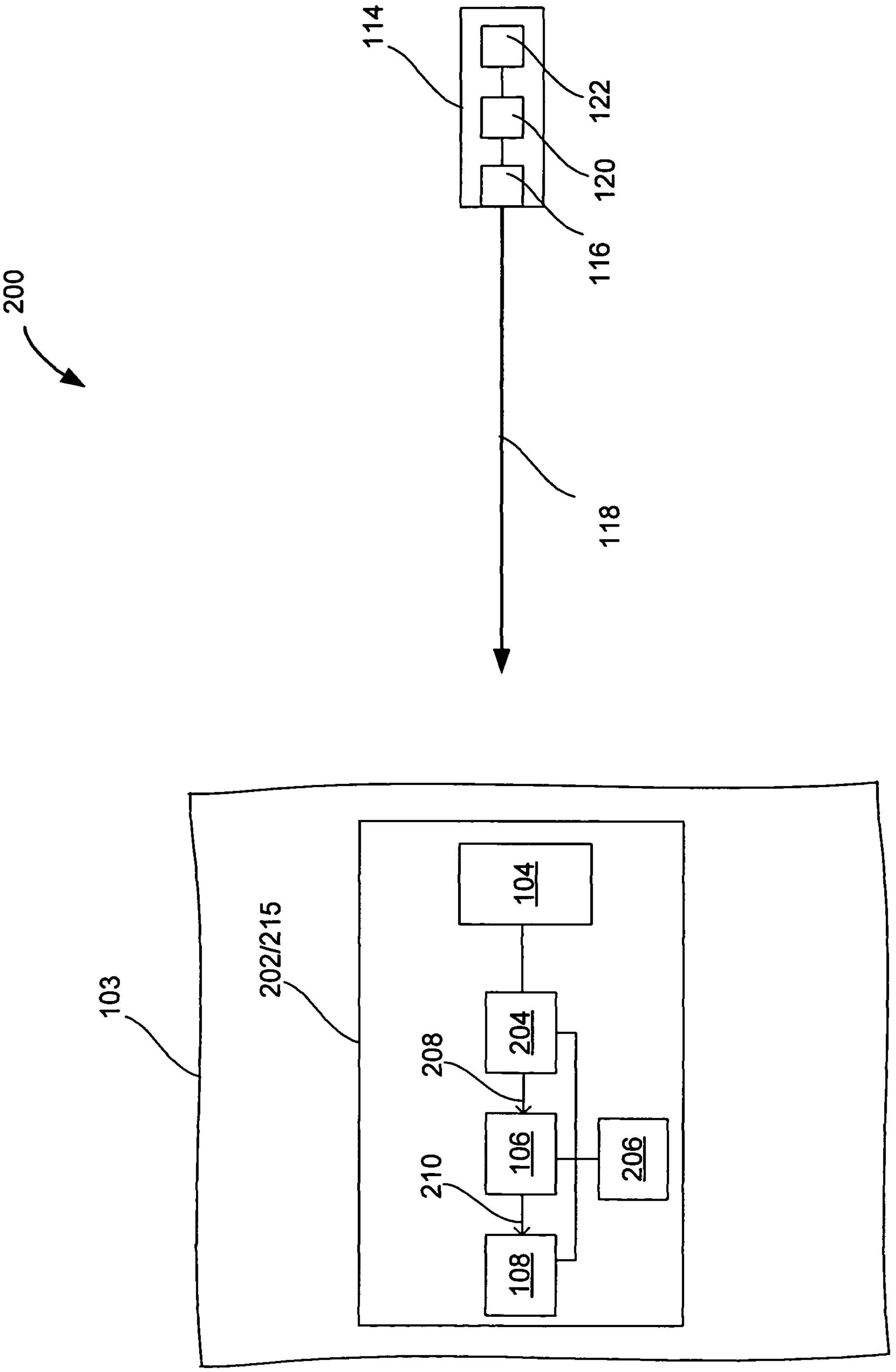
FIG. 2 is a functional block diagram of an embodiment of a system including an energy-storage device that stores electrical energy prior to transmission to a power conditioning unit.

FIG. 2 is a functional block diagram of an embodiment of a system 200 including an energy-storage device that stores electrical energy prior to transmission to a power conditioning unit. The system includes a biocompatible apparatus 202 including an optical-electrical converter 104, an energy-storage device 204, and a power conditioning unit 106 disposed within the living subject 103 and coupled to the energy-storage device 204 to receive electrical energy therefrom. The components of the apparatus 202 may be collectively or individually housed in a biocompatible protective packaging 215 that is configured the same or similarly to the biocompatible protective packaging 115 of FIG. 1A. The energy-storage device 204 may be, for example, a capacitive device or a battery. The system 200 further includes control electrical circuitry 206 operably coupled to the energy-storage device 204, the power conditioning unit 106, and the at least one device 108. The control electrical circuitry 206 is configured to control distribution of electrical energy from the energy-storage device 204 and the operation of the power conditioning unit 106 and at least one device 108.

In operation, the optical power source 116 of the external optical power device 114 outputs the one or more optical power signals 118 that are transmitted transdermally into the living subject 103 and received by the optical-electrical converter 104. The optical-electrical converter 104 converts the one or more optical power signals 118 to electrical energy that is stored by the energy-storage device 204. The energy-storage device 204 transmits one or more electrical power signals 203 to the power conditioning unit 106 that selectively conditions the one or more electrical power signals 208 to generate one or more conditioned electrical power signals 210 that power the at least one device 108.

In some embodiments, the power conditioning unit 106 of the apparatus 202 may be configured to selectively condition the electrical energy received from the energy-storage device 204 in response to one or more conditioning signals transmitted transdermally into the living subject 103.

In the embodiment illustrated in FIG. 2, the power-conditioning unit 106 conditions electrical energy received from the energy-storage device 204. However, in an embodiment, the power conditioning unit 106 may condition the electrical energy generated by the optical-electrical converter 104. The conditioned electrical energy may be stored by the energy-storage device 204 and output to the at least one device 108 as one or more electrical power signals having a selected waveform that power the at least one device 108.

Figure 3:
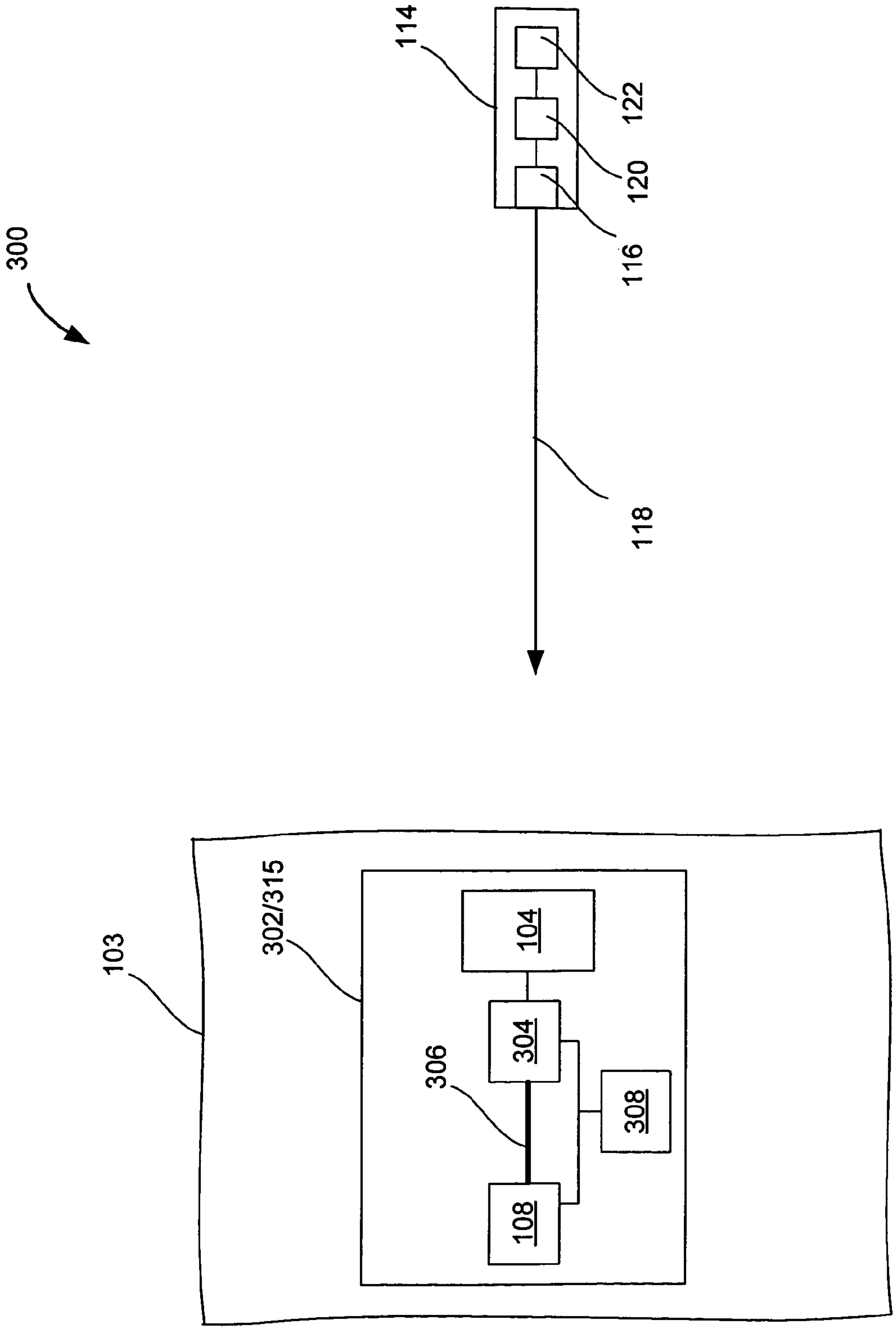
FIG. 3 is a functional block diagram of an embodiment of a system including an energy-storage device that routes power to at least one device via at least one power exporter.

FIG. 3 is a functional block diagram of an embodiment of a system 300 including an energy-storage device that routes power to at least one device via at least one power exporter. The system 300 includes a biocompatible apparatus 302 disposed within the living subject 103 and having an optical-electrical converter 104, an energy-storage device 304 (e.g., a capacitive device or a battery), at least one device 108 coupled to the energy-storage device 304 via at least one power exporter 306, and control electrical circuitry 308 configured to control distribution of electrical power from the energy-storage device 304 and the operation of the at least one device 108. The components of the apparatus 302 may be collectively or individually housed in a biocompatible protective packaging 315 that is configured the same or similarly to the biocompatible protective packaging 115 of FIG. 1A.

In operation, the optical power source 116 of the external optical power device 114 outputs the one or more optical power signals 118 that are transmitted transdermally into the living subject 103 and received by the optical-electrical converter 104. The optical-electrical converter 104 converts the one or more optical power signals 118 to electrical energy that is stored by the energy-storage device 304. The stored electrical energy may be transmitted to the at least one device 108 via the at least one power exporter 306 under the control of the control electrical circuitry 308. For example, the at least one power exporter 306 may be configured as one or more wires. In other embodiments, the at least one power exporter 306 may include an electrical-optical converter that converts the stored electrical energy and transmits it as one or more optical power signals via one or more optical waveguides (e.g., one or more optical fibers), or an electrical-acoustic converter that converts the stored electrical energy to acoustic energy and transmits it as one or more acoustic power signals via an ultrasound transmitter. The control electrical circuitry 308 may further control the operation of the at least one device 108.

In another embodiment, a power conditioning unit may be coupled to the at least one power exporter 306 and the energy-storage device 304. In such an embodiment, the power conditioning unit may be configured to selectively condition at least a portion of the electrical energy received from the energy-storage device 304 and transmit the conditioned electrical energy to the at least one power exporter 306 for exporting to the at least one device 108.

Figure 4:
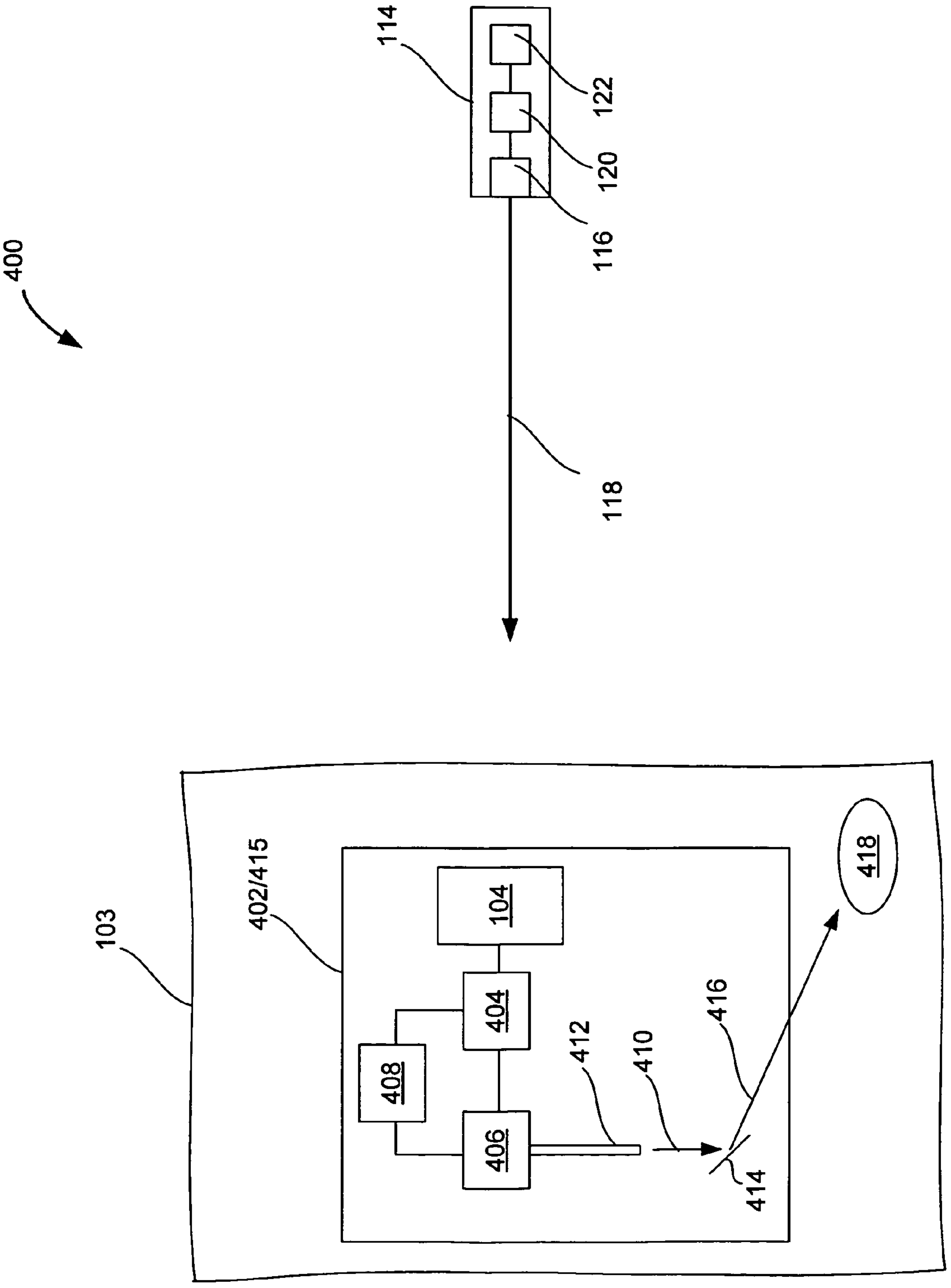
FIG. 4 is a functional block diagram of an embodiment of a system that converts stored electrical energy to optical energy that may be routed to a selected location within a living subject to initiate release of one or more therapeutic drugs.

FIG. 4 is a functional block diagram of an embodiment of a system 400 that converts stored electrical energy to optical energy that may be routed to a selected location within the living subject 103. The system 400 includes a biocompatible apparatus 402 disposed within the living subject and having an optical-electrical converter 104, an energy-storage device 404 that stores electrical energy received from the optical-electrical converter 104, and an electrical-optical converter 406 that converts stored electrical energy to optical energy that can initiate release of a therapeutic drug each of which is disposed within the living subject 103. The components of the apparatus 402 may be housed collectively or individually in a biocompatible protective packaging 415 that is configured the same or similarly to the biocompatible protective packaging 115 of FIG. 1A.

The optical-electrical converter 104 is coupled to the energy-storage device 404 so that the energy-storage device 404 receives electrical energy generated by converting the transdermally transmitted one or more optical power signals 118. The electrical-optical converter 406 is coupled to receive at least a portion of the electrical energy from the energy-storage device 404 and convert the at least a portion of the electrical energy to one or more optical signals 410 (e.g., one or more electromagnetic beams). For example, the electrical-optical converter 406 may include one or more light-emitting devices, such as one or more light emitting diodes or one or more laser diodes. The one or more optical signals 410 may be transmitted to a selected location within the living subject 103 via one or more optical waveguides 412, such as one or more optical fibers. For example, the one or more optical waveguides 412 may be disposed within a vein or other passageway of the living subject 103.

The system 400 further includes control electrical circuitry 408 that is coupled to the energy-storage device 404 and the electrical-optical converter 406. The control electrical circuitry 408 is configured to control distribution of the at least a portion of electrical energy from the energy-storage device 404 to the electrical-optical converter 406 and the operation of the electrical-optical converter 406.

The system 400 may further include a beam director 414 configured to direct the one or more optical signals 410 in a selected direction as one or more beams 416 that are transmissive through the biocompatible protective packaging 415 and through tissue of the living subject 103. For example, the beam director 414 may be a diffractive element or an optical scanner (e.g., a micro-electro-mechanical scanner). The one or more beams 416 may be transmitted through the biocompatible protective packaging 415 to irradiate one or more therapeutic drugs 418 and initiate release thereof. In an embodiment, the one or more beams 416 may be focused using one or more optical elements (e.g., one or more lenses) prior to irradiating the therapeutic drug 418. For example, in an embodiment, the beam director 414 may be a MEMS scanner having a scan plate configured with optical power that can focus the one or more optical signals 410 and also scan the one or more optical signals 410 across a field-of-view as the one or more beams 416.

In operation, the optical power source 116 of the optical power device 114 outputs one or more optical power signals 118 that are transmitted transdermally through the living subject 103, through the biocompatible packaging 415, and received by the optical-electrical converter 104. The optical-electrical converter 104 converts the one or more optical power signals 118 to electrical energy that is received by and stored by the energy-storage device 404. Under control of the control electrical circuitry 408, at least a portion of the electrical energy stored by the energy-storage device 404 is transmitted to the electrical-optical converter 406, which converts it to the one or more optical signals 410. The one or more optical signals 410 are guided by and output from the optical waveguide 412. The beam director 414 directs the one or more optical signals 410 to irradiate the one or more therapeutic drugs 418 to initiate release of one or more drugs or may irradiate an internal region of the living subject 103 (e.g., to destroy a selected internal region of the living subject 103).

Figure 5:
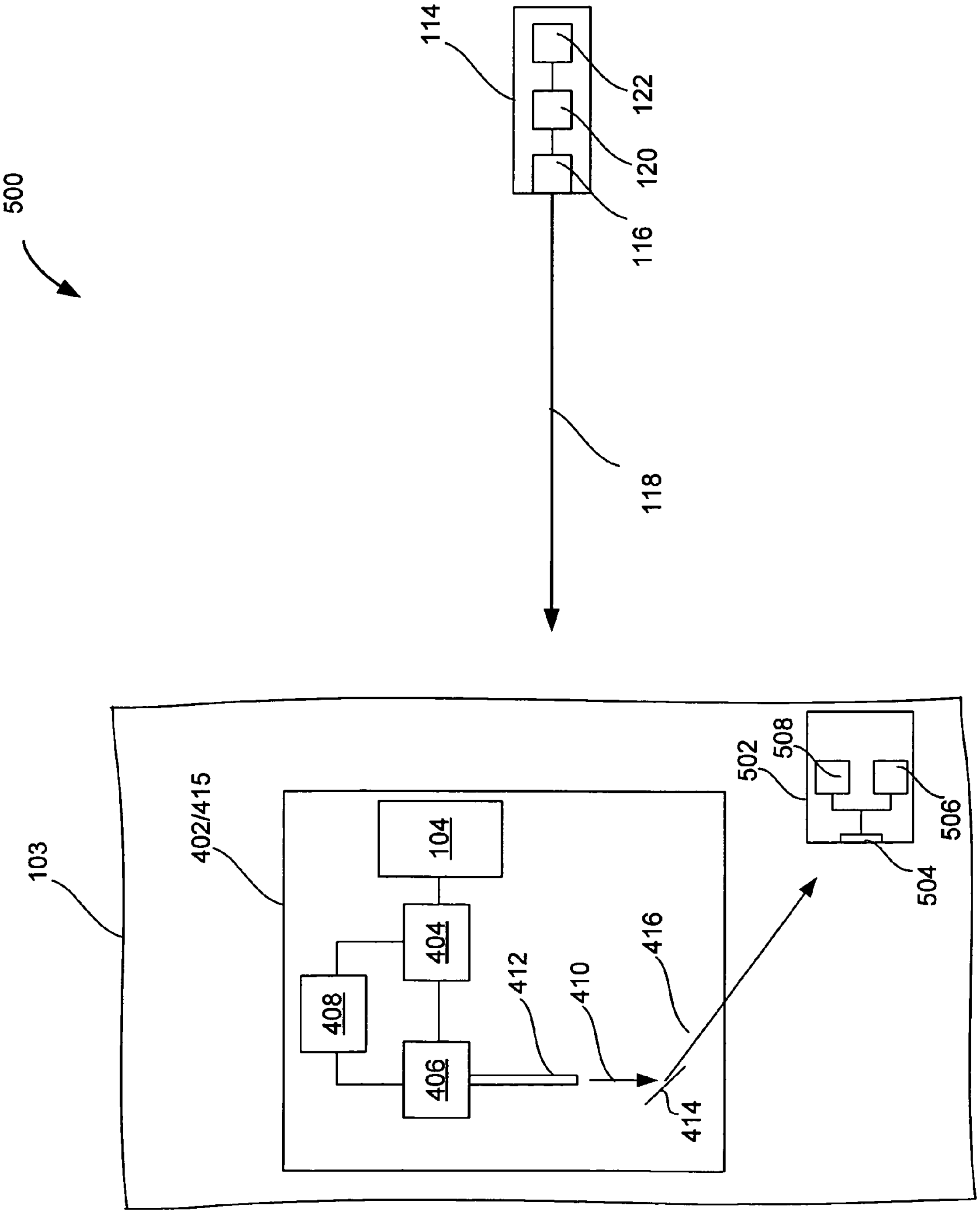
FIG. 5 is a functional block diagram of an embodiment of a system that converts stored electrical energy to optical energy that may be routed to a selected location within a living subject to power at least one device disposed in the living subject.

FIG. 5 is a functional block diagram of an embodiment of a system 500 that converts stored electrical energy to optical energy that may be routed to a selected location within the living subject 103 to power at least one device disposed in the living subject 103. The system 500 employs the same biocompatible apparatus 402 shown in the system 400 depicted in FIG. 4. However, the one or more optical signals 416 may be used to power at least one device 502 disposed in the living subject.

The at least one device 502 may be configured as at least one of a drug delivery device, a micro-electro-mechanical device, a bone extension device, a biosensor, a heart pacemaker, a heart stimulator, a neurostimulator, or other suitable biomedical device. The at least one device 502 includes an optical-electrical converter 504 (e.g., one or more photodiodes), control electrical circuitry 506, and a power system 508.

In operation, the optical-electrical converter 504 receives and converts the one or more optical signals 416 output from the beam director 414 to one or more electrical power signals. The one or more electrical power signals power the power system 508 of the at least one device 502.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electromechanical systems having a wide range of electrical components such as hardware, software, firmware, or virtually any combination thereof, and a wide range of components that may impart mechanical force or motion such as rigid bodies, spring or torsional bodies, hydraulics, and electro-magnetically actuated devices, or virtually any combination thereof. Consequently, as used herein "electromechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having"

should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A method, comprising:

receiving one or more optical power signals, that are transmitted transdermally into a living subject, with an optical-electrical converter disposed within the living subject;

converting the one or more optical power signals into electrical energy using the optical-electrical converter within the living subject; and within the living subject, selectively conditioning at least a portion of the electrical energy into one or more electrical power signals having a frequency selected to limit interference with other biomedical devices disposed in the living subject in response to receiving one or more conditioning signals from at least one device disposed within the living subject.

2. The method of claim 1, wherein receiving one or more optical power signals, that are transmitted transdermally into a living subject, with an optical-electrical converter disposed within the living subject includes receiving the one or more optical power signals with one or more photodiodes.

3. The method of claim 1, wherein selectively conditioning at least a portion of the electrical energy into one or more electrical power signals includes converting at least a portion of the electrical energy from an AC waveform to a DC waveform.

4. The method of claim 1, wherein selectively conditioning at least a portion of the electrical energy into one or more electrical power signals includes converting at least a portion of the electrical energy from a DC waveform to an AC waveform.

5. The method of claim 1, wherein selectively conditioning at least a portion of the electrical energy into one or more electrical power signals includes converting at least a portion of the electrical energy from a first DC waveform to a second DC waveform.

6. The method of claim 1, wherein selectively conditioning at least a portion of the electrical energy into one or more electrical power signals includes converting at least a portion of the electrical energy from a first AC waveform to a second AC waveform.

7. The method of claim 1, further comprising:

receiving the one or more conditioning signals, which includes one or more optical conditioning signals, that are transmitted transdermally into the living subject;

converting the one or more optical conditioning signals into one or more electrical conditioning signals using an optical-electrical signal converter; and wherein selectively conditioning the at least a portion of the electrical energy into one or more electrical power signals occurs in response to receiving the one or more electrical conditioning signals.

8. The method of claim 7, wherein the optical-electrical signal converter and the optical-electrical converter are the same device.

9. The method of claim 8, further comprising powering the at least one device disposed within the living subject using the one or more electrical power signals.

10. The method of claim 9, wherein the at least one device includes at least one of a drug delivery device, a micro-electro-mechanical device, a bone extension device, a biosensor, a heart pacemaker, a heart stimulator, or a neurostimulator.

11. The method of claim 1, further comprising powering the at least one device disposed within the living subject using the one or more electrical power signals.

12. The method of claim 1, further comprising storing at least a portion of the electrical energy with an energy-storage device.

13. A method, comprising:

receiving one or more optical power signals, that are transmitted transdermally into a living subject, with an optical-electrical converter disposed within the living subject;

receiving one or more optical conditioning signals that are transmitted transdermally into the living subject;

converting the one or more optical power signals into electrical energy using the optical-electrical converter;

converting the one or more optical conditioning signals into one or more electrical conditioning signals using the optical-electrical signal converter; and selectively conditioning at least a portion of the electrical energy into one or more electrical power signals in response to receiving the one or more electrical conditioning signals.

14. The method of claim 13, wherein the optical-electrical signal converter and the optical-electrical converter are the same device.

15. The method of claim 14, further comprising powering at least one device disposed within the living subject using the one or more electrical power signals.

16. The method of claim 15, wherein the at least one device includes at least one of a drug delivery device, a micro-electro-mechanical device, a bone extension device, a biosensor, a heart pacemaker, a heart stimulator, or a neurostimulator.

17. A method, comprising:

receiving one or more optical power signals, that are transmitted transdermally into a living subject, with an optical-electrical converter disposed within the living subject;

receiving one or more conditioning signals;

converting the one or more optical power signals into electrical energy using the optical-electrical converter; and selectively conditioning at least a portion of the electrical energy into one or more electrical power signals in response to receiving the one or more conditioning signals.

18. The method of claim 17, further comprising powering at least one device disposed within the living subject using the one or more electrical power signals.

19. The method of claim 18, wherein the at least one device includes at least one of a drug delivery device, a micro-electro-mechanical device, a bone extension device, a biosensor, a heart pacemaker, a heart stimulator, or a neurostimulator.

20. A method, comprising:

receiving one or more optical power signals, that are transmitted transdermally into a living subject, with an optical-electrical converter disposed within the living subject;

converting the one or more optical power signals into electrical energy using the optical-electrical converter; and selectively conditioning at least a portion of the electrical energy into one or more electrical power signals by selectively conditioning the at least a portion of the electrical energy into one or more electrical power signals in response to receiving one or more conditioning signals from at least one device disposed within the living subject.

21. The method of claim 20, further comprising powering at least one device disposed within the living subject using the one or more electrical power signals.

22. The method of claim 21, wherein the at least one device includes at least one of a drug delivery device, a micro-electro-mechanical device, a bone extension device, a biosensor, a heart pacemaker, a heart stimulator, or a neurostimulator.

* * * * *